(12) United States Patent
Reiley (10) Patent No.: US 7,922,765 B2
(45) Date of Patent: Apr. 12, 2011

(54) SYSTEMS AND METHODS FOR THE FIXATION OR FUSION OF BONE

(75) Inventor: Mark A. Reiley, Piedmont, CA (US)

(73) Assignee: SI-Bone, Inc., San Jose, CA (US)

( * ) Notice: Subject to any disclaimer, the term of this patent is extended or adjusted under 35 U.S.C. 154(b) by 491 days.

(21) Appl. No.: 11/136,141

(22) Filed: May 24, 2005

(65) Prior Publication Data

US 2006/0036322 A1    Feb. 16, 2006

Related U.S. Application Data

(63) Continuation-in-part of application No. 10/914,629, filed on Aug. 9, 2004, now abandoned.

(51) Int. Cl.
*A61F 2/44*      (2006.01)

(52) U.S. Cl. .................. 623/17.11; 606/279; 623/17.16

(58) Field of Classification Search ............ 606/61, 606/69–73, 246–279, 68 A; 623/17.11–17.16
See application file for complete search history.

(56) References Cited

U.S. PATENT DOCUMENTS

| | | | |
|---|---|---|---|
| 4,344,190 A | 8/1982 | Lee et al. | |
| 4,501,269 A | 2/1985 | Bagby | |
| 4,657,550 A * | 4/1987 | Daher | 623/17.11 |
| 4,834,757 A | 5/1989 | Brantigan | |
| 4,961,740 A | 10/1990 | Ray et al. | |
| 5,139,498 A | 8/1992 | Astudillo | |
| 5,298,254 A | 3/1994 | Prewett et al. | |
| 5,569,249 A | 10/1996 | James et al. | |
| 5,593,409 A | 1/1997 | Michelson | |
| 5,609,636 A | 3/1997 | Kohrs et al. | |
| 5,669,909 A | 9/1997 | Zdeblick et al. | |
| 5,868,749 A * | 2/1999 | Reed | 606/76 |
| 5,968,047 A * | 10/1999 | Reed | 606/76 |
| 6,010,507 A * | 1/2000 | Rudloff | 606/72 |
| 6,053,916 A | 4/2000 | Moore | |
| 6,096,080 A * | 8/2000 | Nicholson et al. | 623/17.16 |
| 6,210,442 B1 * | 4/2001 | Wing et al. | 623/17.11 |
| 6,241,732 B1 * | 6/2001 | Overaker et al. | 606/72 |
| 6,270,528 B1 * | 8/2001 | McKay | 623/17.11 |
| 6,517,541 B1 | 2/2003 | Sesic | |
| 6,595,998 B2 * | 7/2003 | Johnson et al. | 606/90 |
| 6,602,293 B1 | 8/2003 | Biermann et al. | |
| 6,605,090 B1 * | 8/2003 | Trieu et al. | 606/69 |
| 6,666,868 B2 * | 12/2003 | Fallin | 606/73 |
| 6,743,257 B2 * | 6/2004 | Castro | 623/17.16 |

(Continued)

FOREIGN PATENT DOCUMENTS

EP    1287796    3/2003

OTHER PUBLICATIONS

PCT/US08/00202 ISR.

*Primary Examiner* — Eduardo C Robert
*Assistant Examiner* — Christina Negrelli
(74) *Attorney, Agent, or Firm* — Ryan Kromholz & Manion, S.C.

(57) ABSTRACT

Various bone fixation/fusion devices are sized and configured to be placed across fracture fragments or between bones that are to be fused.

4 Claims, 11 Drawing Sheets

U.S. PATENT DOCUMENTS

| | | |
|---|---|---|
| 2001/0049529 A1* | 12/2001 | Cachia et al. .................. 606/72 |
| 2002/0049497 A1* | 4/2002 | Mason ....................... 623/17.11 |
| 2002/0128652 A1* | 9/2002 | Ferree ............................ 606/61 |
| 2003/0065332 A1* | 4/2003 | TenHuisen et al. ............. 606/73 |
| 2003/0233147 A1* | 12/2003 | Nicholson et al. ......... 623/17.16 |
| 2004/0073314 A1 | 4/2004 | White et al. |
| 2004/0106925 A1 | 6/2004 | Culbert |
| 2004/0117022 A1* | 6/2004 | Marnay et al. ............ 623/17.16 |
| 2004/0147929 A1 | 7/2004 | Biedermann et al. |
| 2005/0033435 A1* | 2/2005 | Belliard et al. ........... 623/17.14 |
| 2006/0129247 A1 | 6/2006 | Brown et al. |
| 2006/0293662 A1 | 12/2006 | Boyer et al. |

* cited by examiner

SYSTEMS AND METHODS FOR THE FIXATION OR FUSION OF BONE

RELATED APPLICATIONS

This application is a continuation-in-part of U.S. patent application Ser. No. 10/914,629, filed Aug. 9, 2004 now abandoned.

FIELD OF THE INVENTION

This application relates generally to the fixation of bone.

BACKGROUND OF THE INVENTION

Many types of hardware are available both for fracture fixation and for the fixation of bones that are to fused (arthrodesed).

Metal and absorbable screws are routinely used to fixate bone fractures and osteotomies. It is important to the successful outcome of the procedure that the screw is able to generate the compressive forces helpful in promoting bone healing.

SUMMARY OF THE INVENTION

The invention provides bone fixation/fusion devices and related methods for stabilizing bone segments, which can comprise parts of the same bone (e.g., fracture fixation) or two or more individual bones (e.g., fusion). The systems and methods include a fixation/fusion device adapted for placement in association with bone segments.

In one embodiment, at least a portion of the device includes a region permitting bony in-growth and/or through-growth.

In one embodiment, the device includes a first region of essentially non-resorbable material and a second region of essentially resorbable material.

In one embodiment, the device includes a region that couples to with another bone fixation/fusion device to form a composite device.

In one embodiment, the device includes at least one stabilization element and/or anti-rotational element.

The bone fixation/fusion device can take various shapes and have various cross-sectional geometries. The device can have, e.g., a generally curvilinear (i.e., round or oval) cross-section, or a generally rectilinear cross section (i.e., square or rectangular or triangular), or combinations thereof. The bone fixation/fusion device can be either elongated, having, e.g., a round or triangular or oval cross-section; or, alternatively, possess a flattened, "wafer" configuration, having, e.g., a rectangular, square, triangular, or disc shape.

DESCRIPTION OF THE PREFERRED EMBODIMENT

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

Figure 1A:
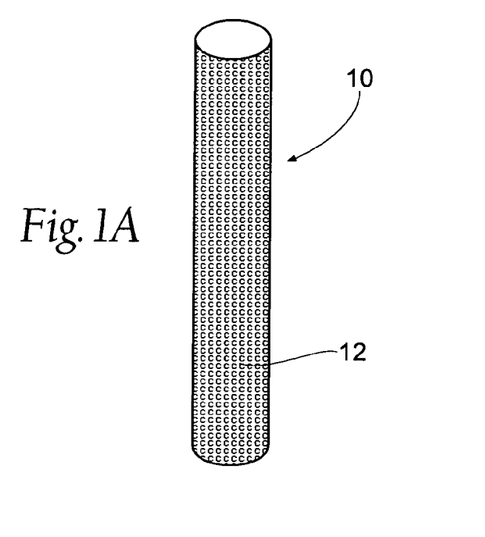
FIGS. 1A and 1B are perspective alternative views of a bone fixation/fusion device having a bony in-growth and/or through-growth region of a mesh configuration.
Figure 1B:
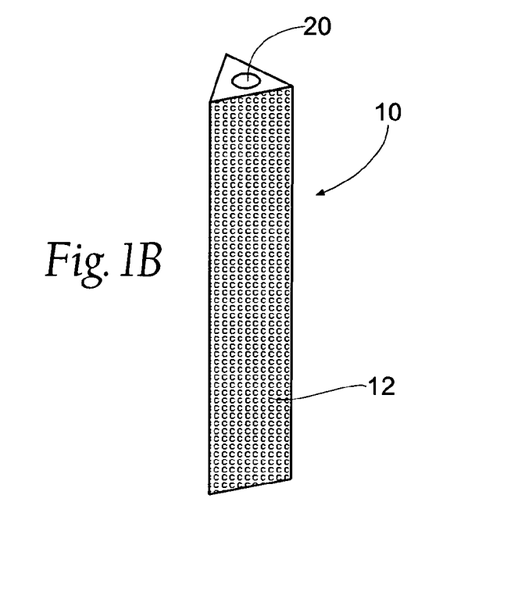

FIGS. 1A and 1B show representative alternative configurations of a device 10 sized and configured for the fixation of bone fractures (i.e., fixation of parts of the same bone) or for the fixation of bones which are to be fused (arthrodesed) (i.e. fixation of two or more individual bones that are adjacent and/or jointed). For the sake of shorthand, the device will sometimes be called a bone fixation/fusion device, to indicate that it can perform a fixation function between two or more individual bones), or a fusion function between two or more parts of the same bone, or both functions. As used herein, "bone segments" or "adjacent bone regions" refer to either situation, i.e., a fracture line in a single bone or a space between different bone segments.

In the embodiments shown in FIGS. 1A and 1B, the bone fixation/fusion device 10 comprises an elongated, stem-like structure. The device 10 can be formed—e.g., by machining, molding, or extrusion—from a material usable in the prosthetic arts, including, but not limited to, titanium, titanium alloys, tantalum, chrome cobalt, surgical steel, or any other total joint replacement metal and/or ceramic, sintered glass, artificial bone, any uncemented metal or ceramic surface, or a combination thereof. Alternatively, the device 10 may be formed from a suitable durable biologic material or a combination of metal and biologic material, such as a biocompatible bone-filling material. The device 10 may be molded from a flowable biologic material, e.g., acrylic bone cement, that is cured, e.g., by UV light, to a non-flowable or solid material.

The bone fixation/fusion device 10 can take various shapes and have various cross-sectional geometries. The device 10 can have, e.g., a generally curvilinear (i.e., round or oval) cross-section—as FIG. 1A shows—or a generally rectilinear cross section (i.e., square or rectangular or triangular—as FIG. 1B shows for purposes of illustration), or combinations thereof. As will be described in greater detail later (see, e.g., FIGS. 21A to 21F), instead of being shaped like an elongated stem, the body of the bone fixation/fusion device 10 can be less elongated and form more of a flattened, "wafer" configuration, having, e.g., a rectangular, square, or disc shape.

Figure 2:
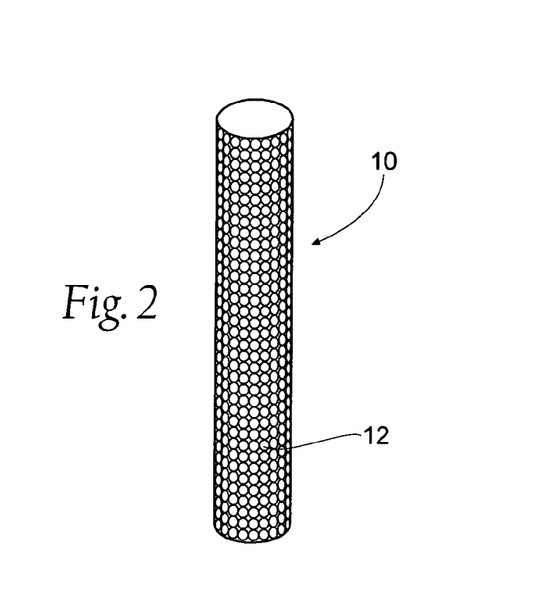
FIG. 2 is a perspective view of an alternative embodiment of a bone fixation/fusion device having a bony in-growth and/or through-growth region of a beaded configuration.
Figure 3:
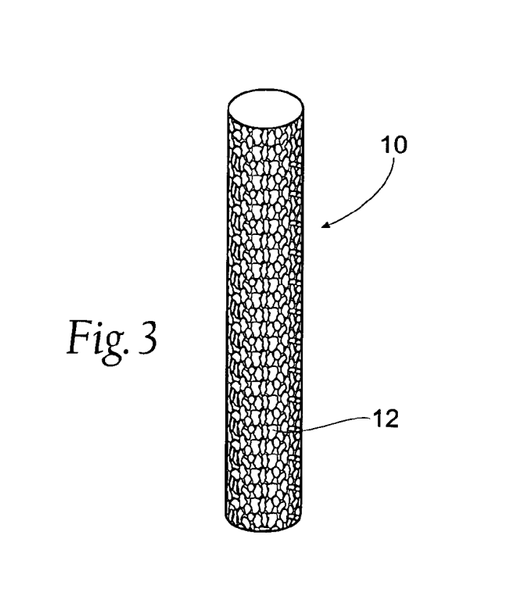
FIG. 3 is a perspective view of an alternative embodiment of a bone fixation/fusion device having a bony in-growth and/or through-growth region of a trabecular configuration.

As FIGS. 2 and 3 show, the bone fixation/fusion device 10 desirably includes a region 12 formed along at least a portion of its length to promote bony in-growth onto or into surface of the device 10 and/or bony growth entirely through all or a portion of the device 10.

The region 12 can comprise, e.g., through holes, and/or various surface patterns, and/or various surface textures, and/or pores, or combinations thereof. The device 10 can be coated or wrapped or surfaced treated to provide the bony in-growth or through-growth region 12, or it can be formed from a material that itself inherently possesses a structure conducive to bony in-growth or through-growth, such as a porous mesh, hydroxyapetite, or other porous surface. The device 10 may further be covered with various other coatings such as antimicrobial, antithrombotic, and osteoinductive agents, or a combination thereof. The region 12 may be impregnated with such agents, if desired.

The configuration of the region 12 can, of course, vary. By way of examples, FIG. 1 shows the region 12 as an open mesh configuration; FIG. 2 shows the region 12 as beaded configuration; and FIG. 3 shows the region 12 as a trabecular configuration. Any configuration conducive to bony in-growth and/or bony through-growth will suffice.

Figure 4:
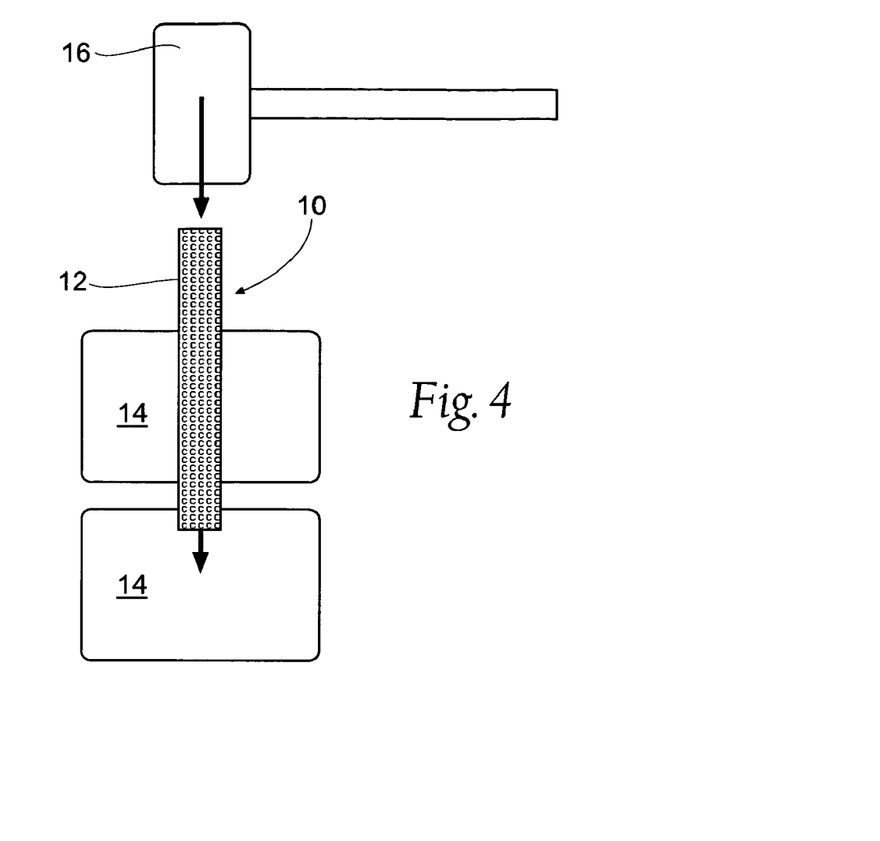
FIG. 4 is a schematic view of a bone fixation/fusion device of the type shown in FIG. 1, being inserted in association with bone across a fracture line or between different bone segments.

In use (see FIGS. 4 and 5), the bone fixation/fusion device 10 is inserted into a space between two adjacent bone surfaces, e.g., into a fracture site in a single bone or between two bones (e.g., adjacent vertebral bodies) which are to be fused together. In FIG. 4, the device 10 is shown being tapped into bone through bone segments 14 (i.e., across a fracture line or between adjacent bones to be fused) with a tap 16. The bone may be drilled first to facilitate insertion of the device 10. The bony in-growth or through-growth region 12 along the surface of the device 10 accelerates bony in-growth or through-growth onto, into, or through the device 10. Bony in-growth or through-growth onto, into, or through the device 10 helps speed up the fusion process or fracture healing time.

Figure 5:
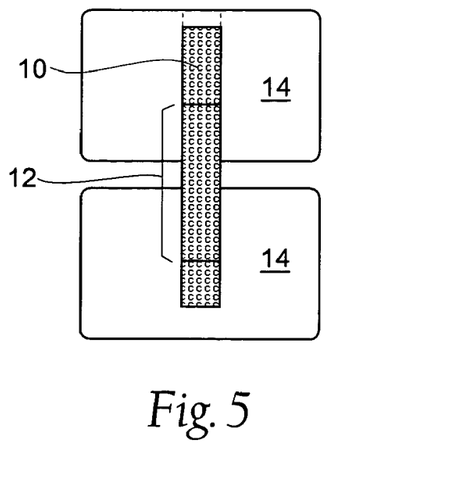
FIG. 5 is a schematic view of a bone fixation/fusion device positioned in association with a fracture line or between different bone segments with a bony in-growth and/or through growth region extending across the fracture line or space between different bone segments.

The bony in-growth or through-growth region 12 may extend along the entire outer surface of the device 10, as shown in FIG. 4, or the bony in-growth or through-growth region 12 may cover just a specified distance on either side of the bone segments or fracture line, as shown in FIG. 5.

The size and configuration of the device 10 can be varied to accommodate the type and location of the bone to be treated as well as individual anatomy.

Figure 6:
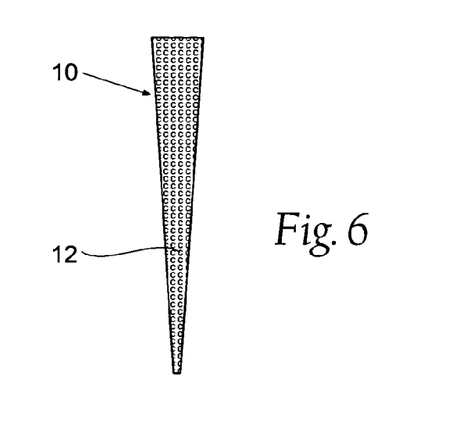
FIG. 6 is a front plan view of an alternative embodiment of a bone fixation/fusion device having a bony in-growth and/or bony through-growth region, in which the device has a conical configuration.
Figure 7:
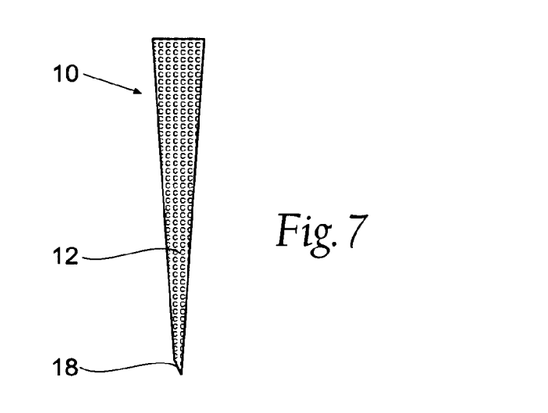
FIG. 7 is front plan view of an alternative embodiment of a bone fixation/fusion device having a bony in-growth and/or through-growth region in which the device has a beveled distal tip.
Figure 8A:
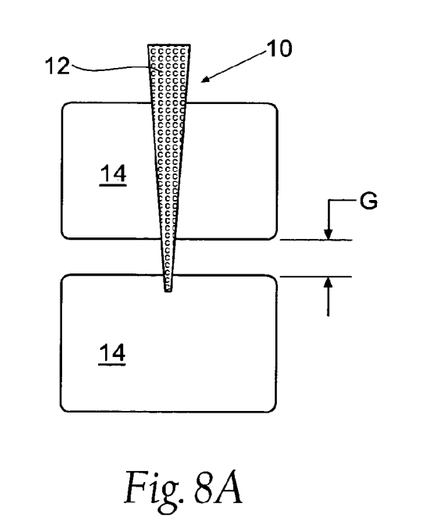
FIGS. 8A and 8B are schematics illustrating the insertion of a bone fixation/fusion device of the type shown in FIG. 6 in association with a fracture line or between different bone segments.
Figure 8B:
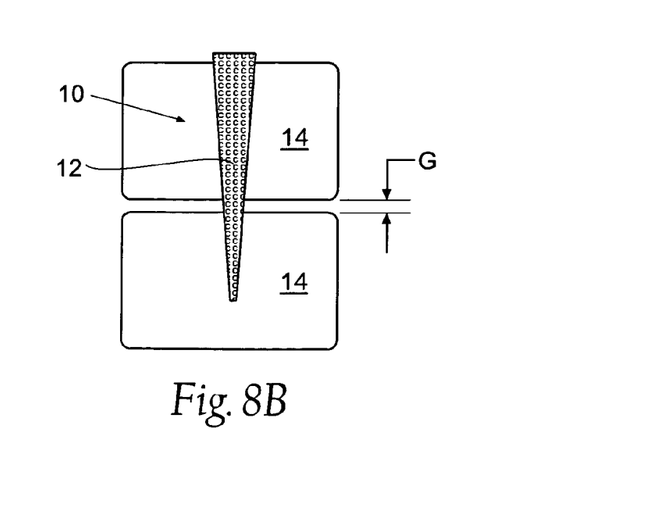

As FIG. 6 shows, the device 10 can be angled or tapered in a conical configuration. The degree of angle can be varied to accommodate specific needs or individual anatomy. A lesser degree of angle (i.e., a more acute angle) decreases the risk of splitting the bone as the device 10 is tapped into the bone or the fracture segments 14. The device 10 may also include a beveled distal tip 18 to further add in insertion of the device 10 into bone, as shown in FIG. 7. As shown in FIGS. 8A and 8B, the conical shape also helps drive the bone segments or fracture fragments together, reducing the gap (G) between the bone segments 14 or fracture segments.

In FIGS. 9 to 12, the device 10 is cannulated, having a central lumen or throughbore 20 extending through it, to assist in the placement of the device 10 within bone. FIG. 1B also shows a cannulated throughbore 20 in a different configuration.

Figure 9:
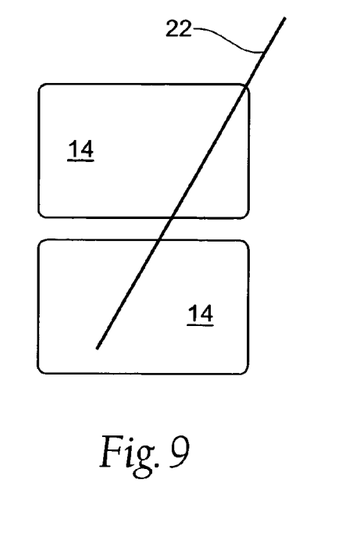
FIG. 9 is a schematic illustrating a guidewire being introduced into bone in association with a fracture line or between different bone segments.
Figure 10:
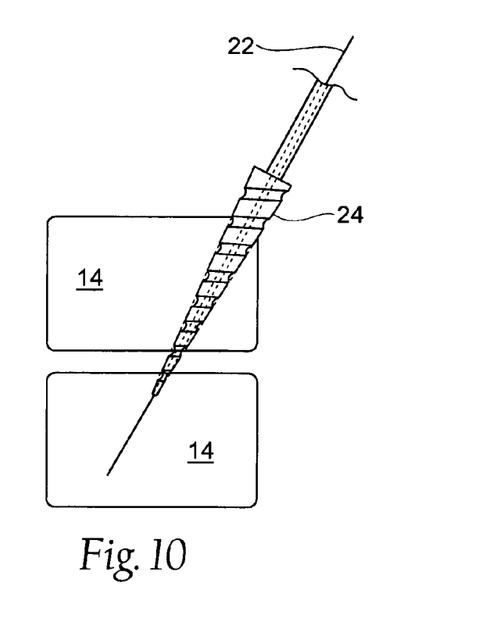
FIG. 10 is a schematic similar to FIG. 9 and illustrating a drill bit being introduced over the guidewire.
Figure 11:
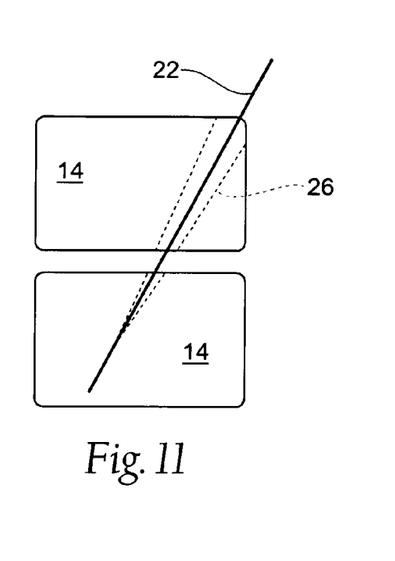
FIG. 11 is a schematic similar to FIG. 10 and illustrating a bore formed in the bone remaining after withdrawal of the drill bit.
Figure 12:
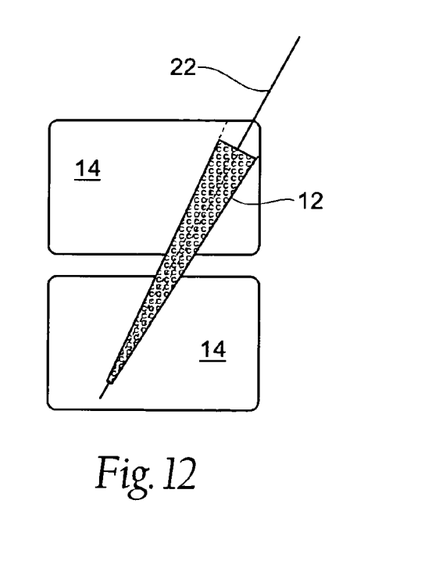
FIG. 12 is a schematic similar to FIG. 11 and illustrating insertion of a bone fixation/fusion device into the pre-formed bore.

In use, the physician can insert a conventional guide pin 22 through the bone segments 14 by conventional methods, as FIG. 9 shows. A cannulated drill bit 24 can then be introduced over the guide pin 22, as seen in FIG. 10. A single drill bit or multiple drill bits 24 can be employed to drill through bone fragments or bone surfaces to create a bore 26 of the desired size and configuration. In the illustrated embodiment, the drill bit 24 is sized and configured to create a conical bore 26 similar in size and configuration to the device 10. The bore 26 is desirably sized and configured to permit tight engagement of the device 10 within the bore 26 and thereby restrict movement of the device 10 within the bore 26. The pre-formed bore 26 may be slightly smaller than the device 10, while still allowing the device 10 to be secured into position within the bore 26 by tapping. As seen in FIG. 11, the drill bit 24 is then withdrawn. The device 10 is then inserted into the bore 26 over the guide pin 22, as FIG. 12 shows. The guide pin 22 is then withdrawn.

Alternatively, the bone fixation/fusion device 10 itself can include screw-like threads along the body for screwing the device into place. In the arrangement, the device 10 be self-tapping. Also in this arrangement, the device 10 can be cannulated for use with a guide pin 22, or it need not be cannulated.

Multiple devices 10 may be employed to provide additional stabilization. While the use of multiple devices 10 will now be described illustrating the use of multiple devices 10 of the same size and configuration, it is contemplated that the devices 10 may also be of different size and/or configuration, e.g., one device 10 is of a cylindrical configuration and a second device 10 is of a conical configuration.

Figure 13:
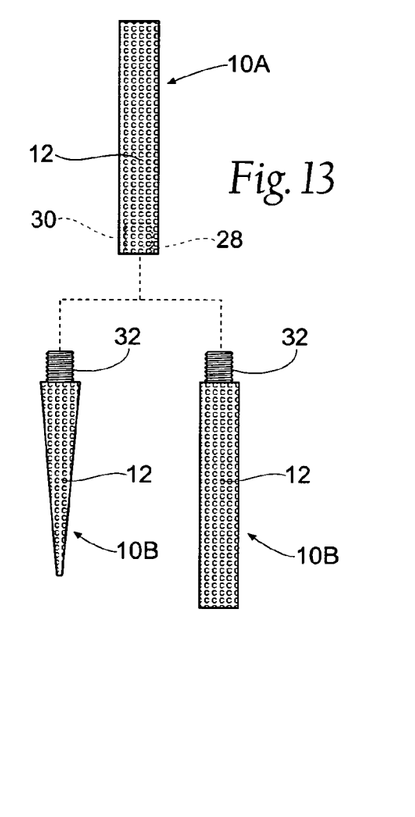
FIG. 13 is an exploded front plan view illustrating the coupling of a pair of bone fixation/fusion by threaded engagement.

In many cases, it may be desirable to couple a series of devices 10 together, e.g., to provide stabilization over a larger surface area. A series of devices 10 may be coupled together be any suitable means, e.g., by a snap fit engagement, or a groove and tab key arrangement, or by a Morse taper fit, or combinations thereof. In one embodiment, a series of devices 10 are coupled by threaded engagement. As illustrated in FIG. 13, a first device 10A includes a recess 28 at one end providing a series of internal threads 30. In the illustrated embodiment, the first device 10 is of a cylindrical configuration, but may be of any desired configuration. The internal threads 30 couple with a series of complementary external threads 32 on a second device 10B of a similar or of a different configuration to couple the first and second devices 10A and 10B together.

Figure 14:
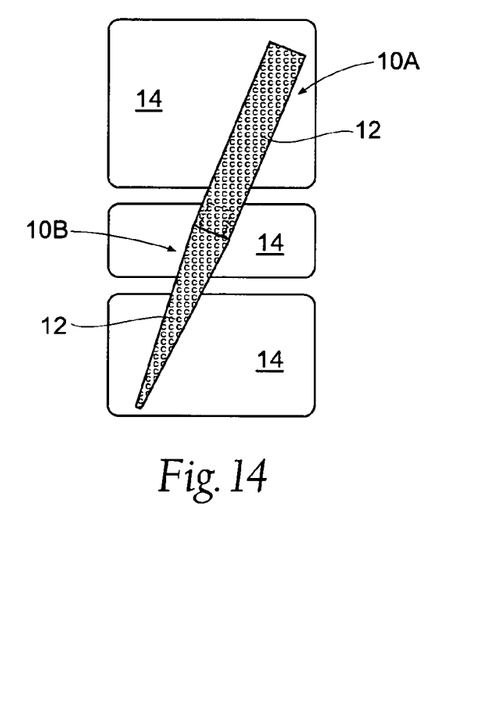
FIG. 14 is a schematic illustrating a pair of bone fixation/fusion devices coupled together and inserted in association with a fracture line or between different bone segments.

The devices 10A and 10B are desirably coupled together prior to being inserted into the pre-formed bore 26. The series of internal and external threads 30 and 32 provide an interlocking mechanism that permits a series of devices 10 to be stacked and connected to cover a larger area or multiple bone segments 14 (e.g., a bone having multiple fractures) and thereby provides additional stabilization, as seen in FIG. 14.

Figure 15:
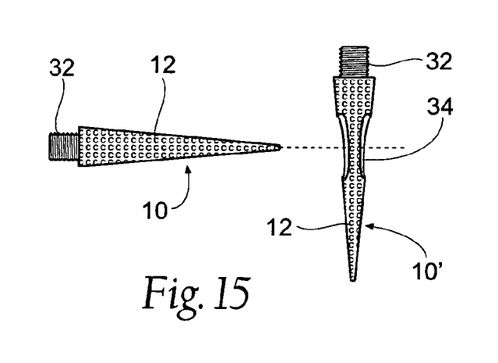
FIG. 15 is a front plan view illustrating passage of a bone fixation/fusion device through a fenestration in another bone fixation/fusion device.

FIG. 15 illustrates another embodiment in which a device 10' includes an opening or fenestration 34 to allow another device 10 to pass through, thereby providing additional stabilization. The fenestration 34 can be sized and configured to permit another device 10 to be passed through the device 10' at virtually any angle. The fenestration 34 can also be sized and configured to limit movement of the second device 10 relative to the second device 10'.

Figure 16:
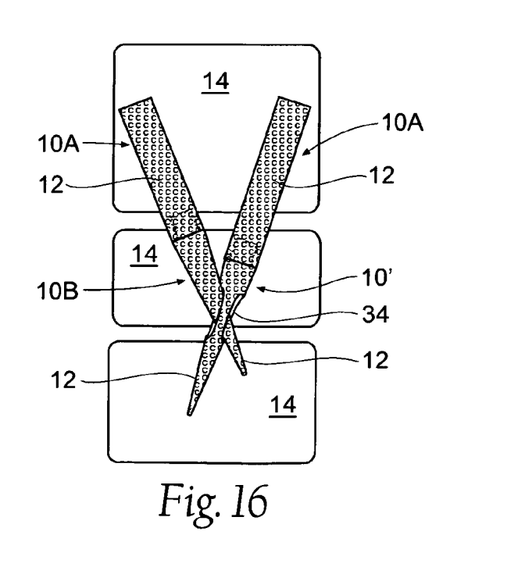
FIG. 16 is a schematic illustrating the placement of a series of bone fixation/fusion devices in bone.

In use, and as shown in FIG. 16, the physician taps a first device 10' having a fenestration 34 through the bone segments. A second device 10 is then inserted (e.g., by tapping) through the fenestration 34 of the first device 10' into place.

It is further contemplated that device 10' may also be adapted for coupling with another device 10A (e.g., by a series of external and internal threads), permitting the devices 10' and 10A to be additionally stacked and connected, as also shown in FIG. 16.

Figure 17:
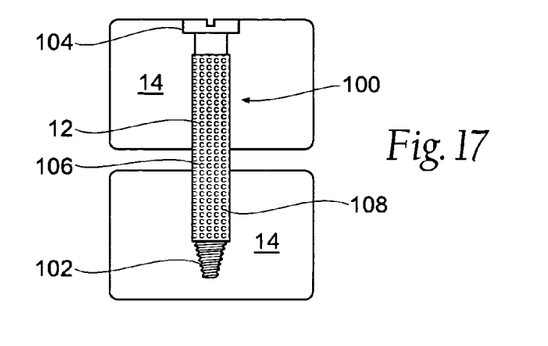
FIG. 17 is a top plan view of a bone fixation/fusion device positioned in association with a fracture line or between different bone segments.

FIG. 17 illustrates an alternative form of a bone fixation/fusion device 100. Similar to the type of bone fixation/fusion device 10 previously described, device 100 includes a body 106 formed of a durable material that is not subject to significant bio-absorption or resorption by surrounding bone or tissue over time. In other words, the body 106 is intended to remain in place for a time sufficient to stabilize the fracture or fusion site. Such materials are well know in the prosthetic arts and include, e.g., titanium, titanium alloys, tantalum, chrome cobalt, surgical steel, or any other total joint replacement metal and/or ceramic, sintered glass, artificial bone, any uncemented metal or ceramic surface, or a combination thereof. Alternatively, the body 106 of the bone fixation/fusion device 100 may be formed from a suitable durable biologic material or a combination of metal and biologic material, such as a biocompatible bone-filling material. The body 106 of the device 100 may be molded from a flowable biologic material, e.g., acrylic bone cement, that is cured, e.g., by UV light, to a non-flowable or solid material.

The body 106 of the device 100 may also include a bony in-growth or through-growth region 108, as already described in association with previous embodiments.

Unlike the bone fixation/fusion device 10, the bone fixation/fusion device 100 includes at least one region associated with the body 106 that, in contrast to the body 106, comprises a material that is subject to more rapid in vivo bio-absorption or resorption by surrounding bone or tissue over time, e.g., within weeks or a few months. The resorbable material can comprise, e.g., polylactic acid (PLA), polyglycolic acid (PGA), poly(lactideglycolide) copolymers, polyanliydrides, cyclode, cirsns, polyorthoasters, n-vinyl alcohol, or other biosorbable polymers or like materials known or recognized in the prosthetic arts as having such characteristics. The bio-absorbable region is intended to facilitate implantation or placement of the body 106, but over time be absorbed to minimize the footprint of the implanted device 100 in the long run.

The bioabsorbable region or regions can possess functionality to aid in the implantation process. For example, as shown the illustrated embodiment, there are two bioabsorbable regions 102 and 104. Region 102 comprises a bioabsorbable screw region 102, which is desirably threaded or otherwise suitably configured to pierce bone and facilitate advancement of the device 100 into bone. The other region 104 comprises a bioabsorbable head region 104, which is desirably configured to mate with an installation instrument, e.g., a screwdriver, to further facilitate advancement and positioning of the bone fixation/fusion device 100 in bone. The bioabsorbable head 104 may also be sized and configured to temporarily anchor the device 100 within bone, e.g., the head 104 may be a slightly larger diameter than the body 106 of the device 100. The bioabsorbable screw portion 102 and head portion 104 are configured to provide an immediate benefit during the initial placement or position of the device 100, but over time be resorbed when they have served their initial purpose during implantation. This leaves the more durable and less resorbable body 106 behind, to serve its longer-term function of stabilizing the fracture or fusion site.

Figure 18A:
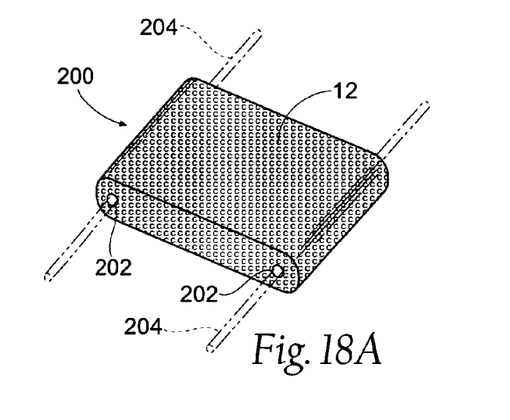
FIG. 18A is a perspective view of an alternative embodiment of a bone fixation/fusion device having a bony in-growth and/or bony through-growth region that extends substantially along the entire device.
Figure 18B:
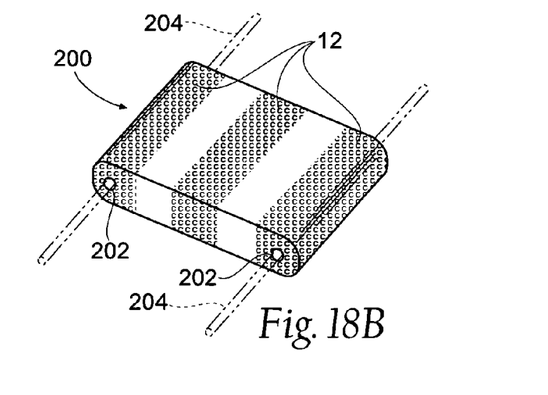
FIG. 18B is a perspective view of a bone fixation/fusion device similar to FIG. 18A and having a bony in-growth and/or bony through-growth region that extends along a portion of the device.

As previously disclosed, a given bone fixation/fusion device can take various shapes and geometries. For example, as shown in FIGS. 18A and 18B, the bone fixation/fusion device 200 possesses a flattened rectangular (or wafer-like) configuration. A region 12 of the device 200 can be textured or treated, as previously described, to provide bony in-growth or through-growth. The bony in-growth or through-growth region 12 may extend along the entire device 200 (see FIG. 18A) or along any portion or portions of the device 200 (see FIG. 18B).

Figure 19:
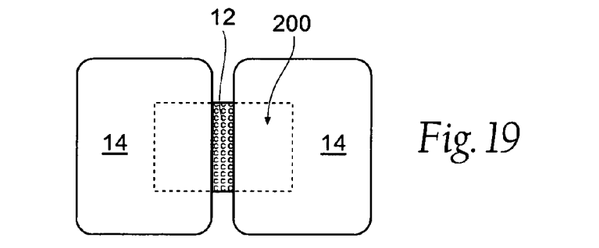
FIG. 19 is a top plan view of the bone fixation/fusion device of FIG. 18A in positioned in association with a fracture line or between different bone segments.
Figure 20:
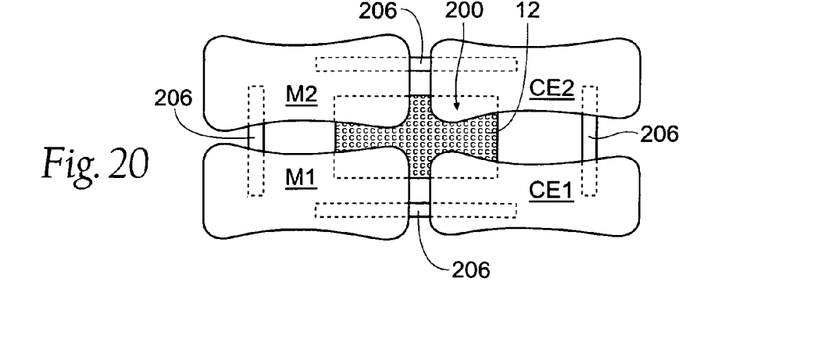
FIG. 20 is a top plan view of the bone fixation/fusion device of FIG. 18A positioned in association with a fracture line or between different bone segments and stabilized by fixation screws.

The bone fixation/fusion device 200 is desirably sized and configured to be positioned to join two or more adjacent bone segments 14 (which can comprise a fracture site, a fusion site, or both), as FIG. 19 shows, to fix and to promote the fusion of the adjacent bone segments 14. The device 200 may also be sized and configured to fix and to promote fusion of multiple bone segments 14 or compound fractures, as FIG. 20 shows. FIG. 20 illustrates placement of the bone fixation/fusion device 200 sized and configured for the fixation and fusion of, for example, a first cuneiform (CE1), a second cuneiform (CE2), a first metatarsal (M1), and a second metatarsal (M2).

As shown in FIG. 20, one or more auxiliary fixation elements, such as conventional orthopedic screws 206, may also be placed within and/or across the bone segments 14 by conventional techniques, to augment the stabilization of the bone segments 14 during the fusion process.

Figures 21A, 21B, 21C, 21D, 21E, 21F:
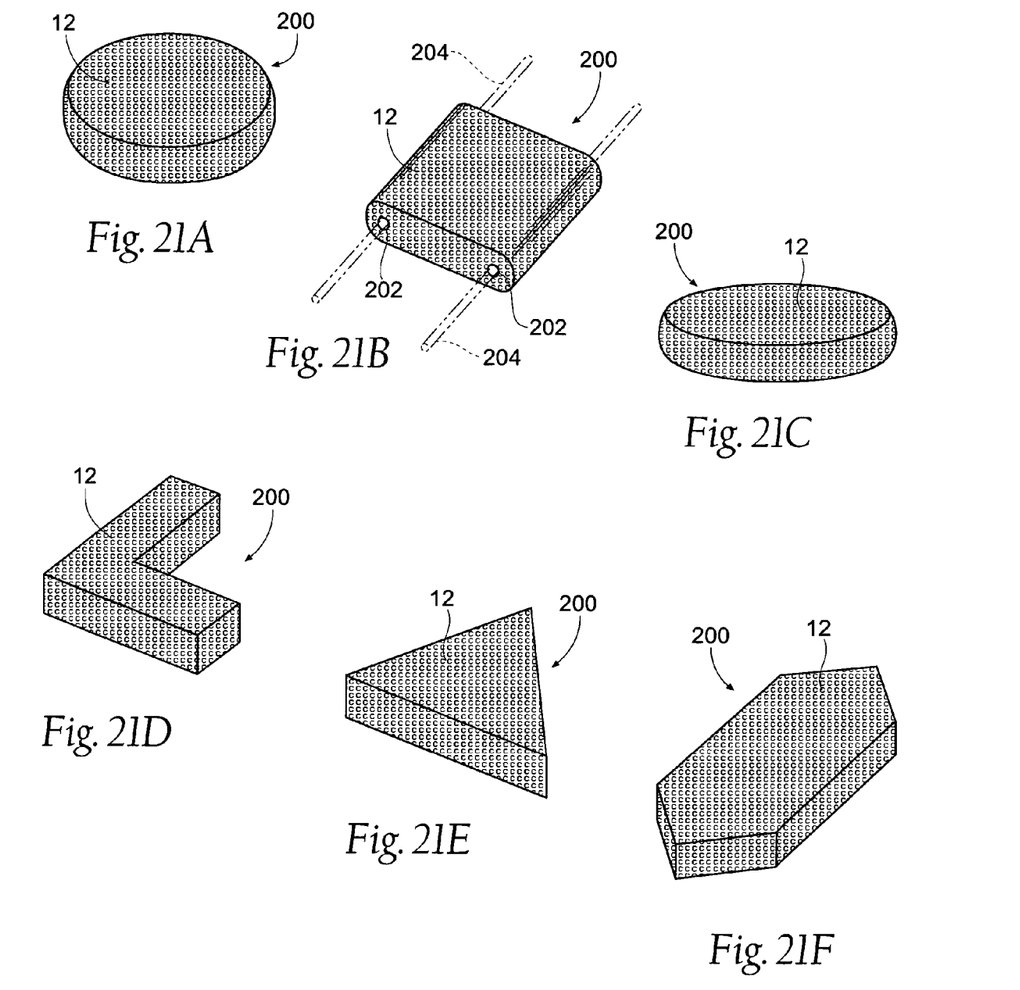
FIGS. 21A to 21F are perspective views illustrating alternative configurations of bone fixation/fusion devices of a type shown in FIG. 18A.

The size and configuration of the bone fixation/fusion device 200 may be modified or adjusted in diverse ways to serve the intended stabilization function in diverse bone locations, bone geometries, or bone types, which are intended to be fused or repaired. The bone fixation/fusion device 200 can come in a family of different pre-established sizes and shapes, or it can be individually sized and configured to meet the requirements of a particular individual's anatomy. For the sake of illustration, by not limitation, a given bone fixation/fusion device 200 may take the form of a disc (FIG. 21A), a square (FIG. 21B), or an oval (FIG. 21C). The height, width, and length of a given bone fixation/fusion device 200 may be varied depending on the specific location and amount of bone to be crossed for stabilization. A given bone fixation/fusion device may possess a symmetric geometry, or an asymmetric or complex geometry—such as an L shape (FIG. 21D), a triangle (FIG. 21E), or rectangle with a triangular ends (FIG. 22F). Any combination of linear or curvilinear or rounded geometries is possible.

Figure 24:
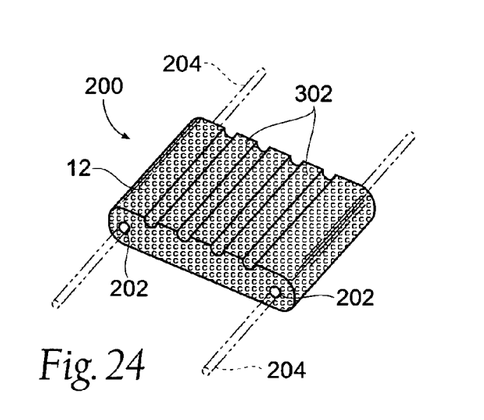
FIG. 24 is a perspective view illustrating an alternative embodiment of the bone fixation/fusion device of a type shown FIG. 18A in which the device includes a series of grooves providing an anti-rotational function.

As before described, a given bone fixation/fusion device can be cannulated to aid in guidance during placement or implantation. For example, as shown in FIGS. 18A and 18B, the device 200 can include a pair of opposing guide bores 202. The guide bores 202 are sized and configured to accommodate passage of guide pins 204, which are secured at the intended site of device placement. Other forms of cannulated devices 200 are shown in FIGS. 21B and 24. In this way, the bone fixation/fusion device 200 can be guided by the pins 204 to the intended bone placement site.

Figure 22A:
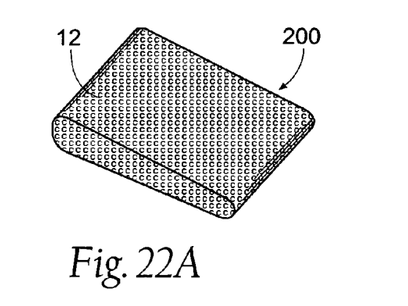
FIGS. 22A and 22B are perspective views illustrating alternative embodiments of the bone fixation/fusion of a type shown in FIG. 18A in which the device is profiled.
Figure 22B:
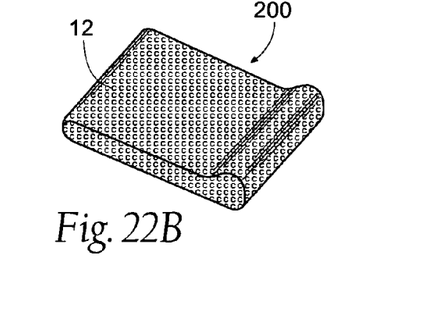

To aid in stabilizing a given bone fixation/fusion device within bone, the device may be profiled. For example, as shown in FIG. 22A, the bone fixation/fusion device 200 may vary in height across its entire length of the device 200, to form a tapered wedge. Alternatively, as shown in FIG. 22B, the bone fixation/fusion device 200 may vary in height at one end only. In these arrangements, the bone fixation/fusion device 200 is desirably positioned with the area of greatest height in the proximal direction, which serves to wedge the device 200 into place within bone.

Figure 23A:
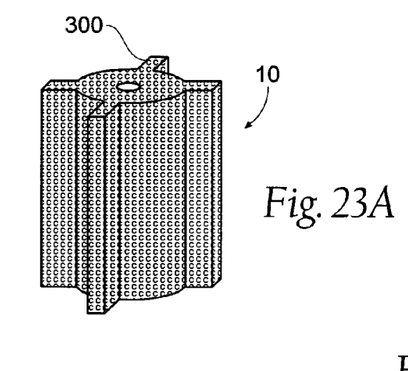
FIGS. 23A and 23B are perspective views illustrating alternative embodiments of the bone fixation/fusion device of a type shown in FIG. 1 with structural elements that provide an anti-rotational function.
Figure 23B:
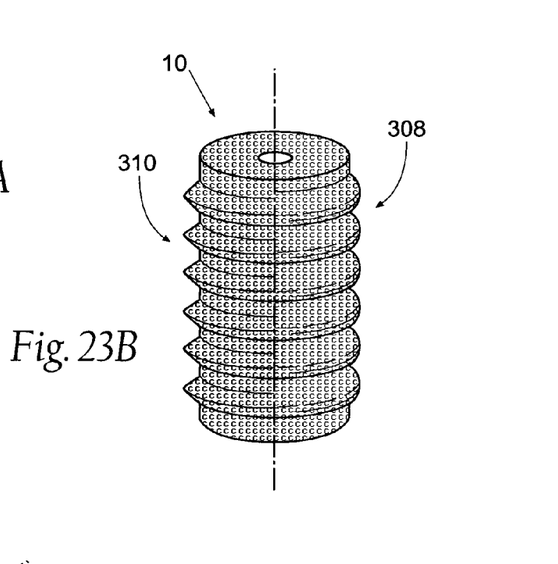
Figure 25:
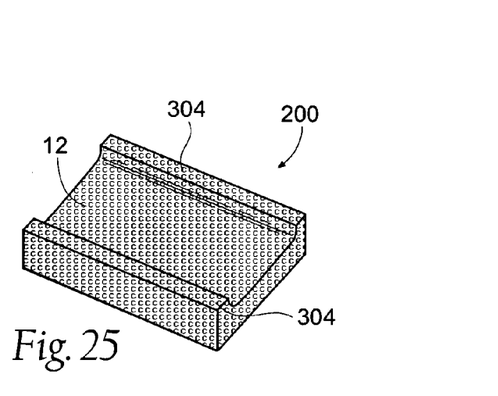
FIG. 25 is a perspective view illustrating an alternative embodiment of the bone fixation/fusion device of a type shown in FIG. 18A in which the device includes a pair of opposing wings providing an anti-rotational function.
Figure 26:
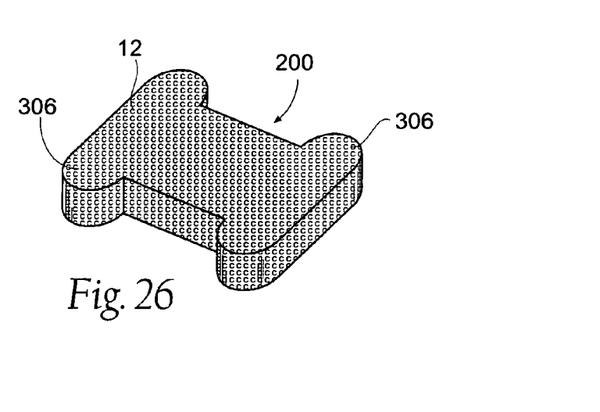
FIG. 26 is a perspective view illustrating an alternative embodiment of the bone fixation/fusion device of FIG. 18A in which the device includes a pair of opposing flanges providing an anti-rotational function.

To also aid in stabilizing a given bone fixation/fusion device within bone, the device can include one or more anti-rotational elements, which further stabilize and secure the device in the desired position within bone. The size and configuration of the anti-rotational elements may vary. For example, the anti-rotational elements may comprise an array of fins 300 projecting from a stem-like device 10 (FIG. 23A), or an array of grooves 302 formed in a rectangular wafer device 200 (FIG. 24), or wings 304 formed in a rectangular wafer device 200 (FIG. 25), or flanges 306 projecting from a wafer device 200 (FIG. 26). The anti-rotational elements can comprise (see FIG. 23B) an array of bumps 308 or surface projections 310 formed on all or a portion of the device, which can be either stem-like or wafer-like in its configuration. Any number of anti-rotational elements, or any configuration of anti-rotational elements, or any combinations of configurations can be provided to serve the functional objective of stabilization.

Figure 27:
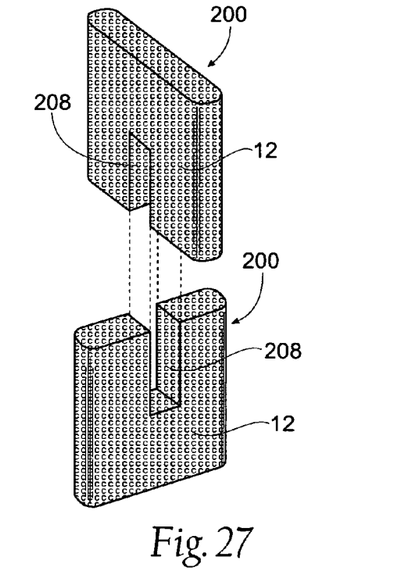
FIG. 27 is an exploded view of a pair of coupled bone fixation/fusion devices that, when fitted together, form a composite bone fixation/fusion device.
Figure 28:
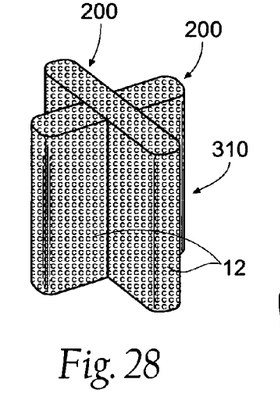
FIG. 28 is an assembled view of the composite bone fixation/fusion device formed from the assembly of the bone fixation/fusion devices shown in FIG. 27.
Figure 29:
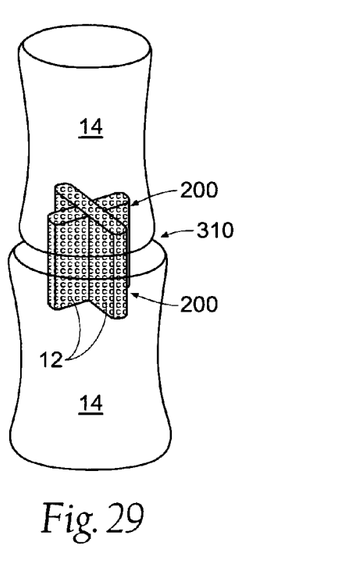
FIG. 29 is a front view of the assembled composite bone fixation/fusion device of FIG. 28 positioned in association with a fracture line or between different bone segments.

As also previously described, two or more bone fixation/fusion devices 200 of the types generally described above may be assembled to form a composite bone fixation/fusion device having a desired size and configuration. For example, in the arrangement shown in FIGS. 27 to 29, the bodies of two bone fixation/fusion devices 200 each have a slot 208. Slot 208 in a first device 200 mates with a like or complementary slot 208 in a second device 200 to permit the assembly of a composite bone fixation/fusion device 310, which has a crossed, anti-rotational configuration for placement across bone segments 14. The crossed relation of the composite bone fixation/fusion device 310 has an increased surface area and adds further stability to the devices 200 in bone during the fusion process.

It will be apparent to one of skill in the art that the location, size, and configuration of the slots 208 may be varied to accommodate specific needs and a specific anatomical location as well as individual anatomy. It is also apparent that other mating configurations, e.g., groove and tab fitments, or snap-fit arrangements, or Morse taper fits, or threaded assemblies, can be use to assemble two or more bone fixation/fusion devices into a composite device 310.

Figure 30:
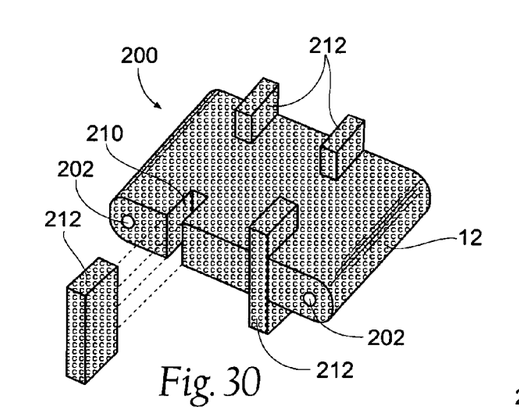
FIG. 30 is a perspective view of an alternative embodiment of the bone fixation/fusion device of a type shown in FIG. 18A with fixation plates.

As shown in FIG. 30, fixation or gripping plates 212 may be fitted to a given bone fixation/fusion device. In the arrangement shown in FIG. 30, the body of the bone fixation/fusion device 200 includes one or more attachment sites 210, e.g., slits or indentations, which are sized and configured to receive a selectively removable fixation or gripping plate 212. When received within the slit 210, the plate 212 extends radially from the device to grip into bone and further secure the device 200 within bone.

Figure 31:
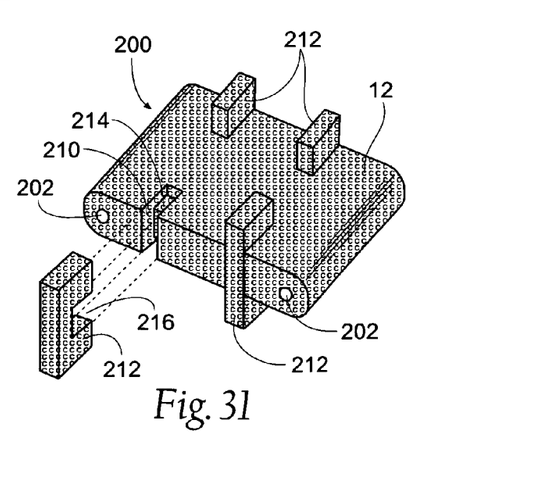
FIG. 31 is a perspective view of an alternative embodiment of the bone fixation/fusion device of FIG. 30.

In an alternative embodiment, shown in FIG. 31, the attachment site 210 can include a tab 214, which mates with a notch 216 in the fixation plate 212 to secure the plate 212 within the device 200.

Other forms of interlocking or nesting configuration can be used. For example, tongue-and-groove fitments, or snap-fit arrangements, or threaded fitments, or Morse taper assemblies can be use to assemble one or more fixation or gripping plates to a bone fixation/fusion device.

The fixation or gripping plate 212 is formed of durable biocompatible metal or bone substitute material, as previously described. In some cases, it may be desirable to provide a bony in-growth surface on at least a portion of the plate 212. Alternatively, the plate 212 may be formed of a bio-absorbable material, as already described.

Figure 32:
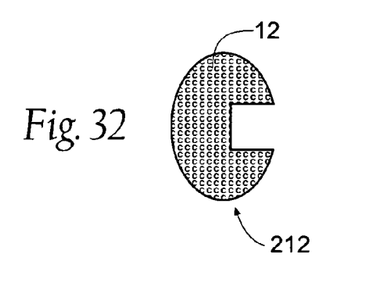
FIG. 32 is a side view of an alternative embodiment of a fixation plate having a rounded configuration.
Figure 33:
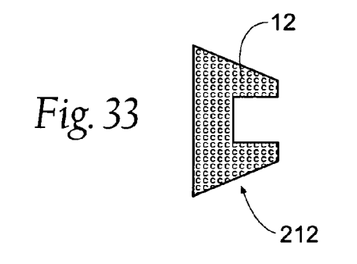
FIG. 33 is a side view of an alternative embodiment of a fixation plate having a tapered configuration.

FIGS. 30 and 31 illustrate embodiments in which the plates 212 present a generally blunt and flat configuration. It will be apparent to one of skill in the art that, however, that the plates 212 may also provide a sharpened or cutting edge or be otherwise sized and configured as necessary to accommodate specific location and individual anatomy. For example, the plate 212 may be rounded (FIG. 32) or tapered (FIG. 33).

Figure 34:
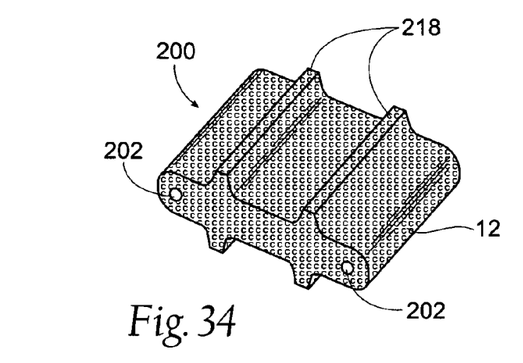
FIG. 34 is a perspective view of an alternative embodiment of the bone fixation/fusion device of a type shown in FIG. 18A providing a series of radially-extending fixation ridges.

FIG. 34 illustrates an alternative embodiment in which one or more fixation ridges 218 extend radially from the bone fixation/fusion device 200. Similar to the fixation plates 212, the ridges 218 may be variously sized and configured so as to grip into bone and further secure the bone fixation/fusion device 200 within bone.

Figure 35A:
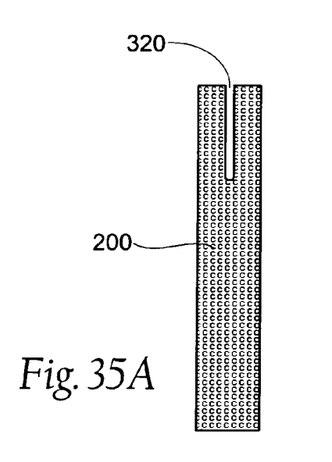
FIGS. 35A and 35B are perspective views of a bone fixation/fusion device having a malleable region that can be flared or expanded to provide fixation and/or anti-rotation resistance.
Figure 35B:
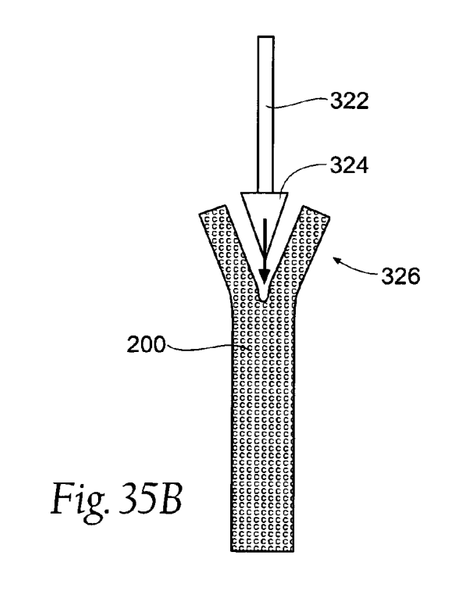

Fixation elements can be formed in situ. For example, as shown in FIG. 35A, a bone fixation/fusion device 200 can include a malleable region 320 that normally presents a low-profile conducive to implantation. As FIG. 35B shows, the profile of the malleable region 320 can be changed in situ after implantation to a radially enlarged or extended profile 326 that provides stabilization or an anti-rotational function to the device 200. In the illustrated embodiment, the malleable region 320 is slotted (see FIG. 35A) to accommodate placement of a wedge tool 324 carried for manipulation by a stylet or cannula 322 (see FIG. 35B). The wedge tool 324 flays apart the slotted malleable region 320 (as FIG. 35B shows), to create the enlarged profile 326 for stabilization and/or rotation resistance.

Figure 36:
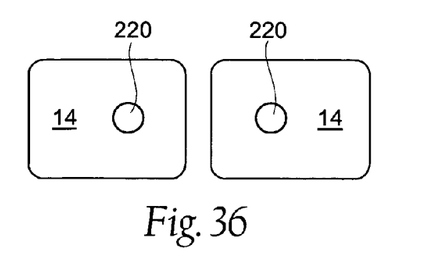
FIG. 36 is a front plan view illustrating the drilling of pilot holes in adjacent bone segments, which can comprise a fracture line in the same bone or different bone segments.

In use, and with reference to FIG. 36, pilot holes 220 are drilled into adjacent bone segments 14 (e.g., along a fracture line in a single bone or between adjacent segments of different bones) by conventional surgical techniques. In the illustrated embodiment, a single pilot hole 220 is drilled into each bone segment 14. It is to be understood that the number and configuration of the pilot holes 220 may vary as necessary or as desired.

Figure 37:
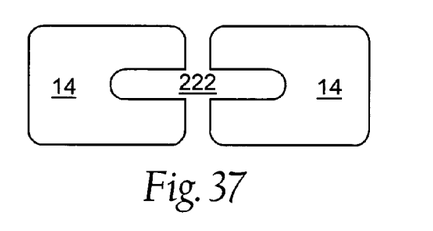
FIG. 37 is a front plan view illustrating a cavity bored between the pilot holes to receive a bone fixation/fusion device.

As shown in FIG. 37, the physician can then then saw, using conventional methods, between the pilot holes 220 to prepare a cavity 222 to receive the device 200.

Figure 38:
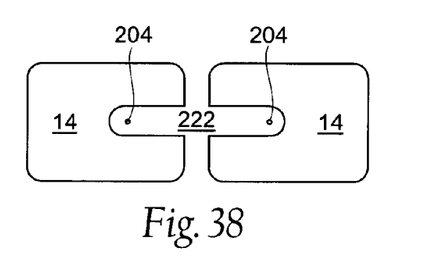
FIG. 38 is a front plan view illustrating the placement of a pair of guide pins within the bored cavity.
Figure 39:
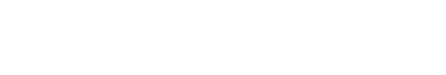
FIG. 39 is a front plan view illustrating the placement of the bone fixation/fusion device into the cavity and removal of the guide pins.

Guide pins 204 may, if desired, be placed at opposing ends of the bored cavity 222, as seen in FIG. 38. In this arrangement, as shown in FIG. 39, the selected bone fixation/fusion device 200 is passed over the guide pins 204 to position the device 200 with the cavity 222. The guide pins 204 may then be removed. In an alternative arrangement, guide pins 204 need not be used, and the device 200 is manually inserted by the physician into the bore cavity 222.

Figure 40:
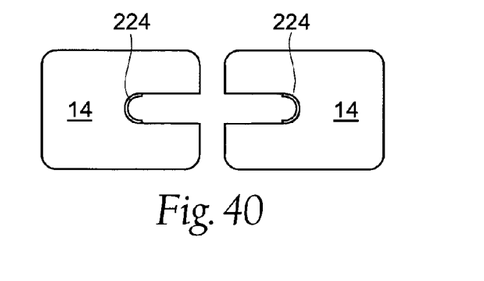
FIG. 40 is a front plan view illustrating the placement of a pair of opposing c-shaped restraints within the bored cavity.
Figure 41:
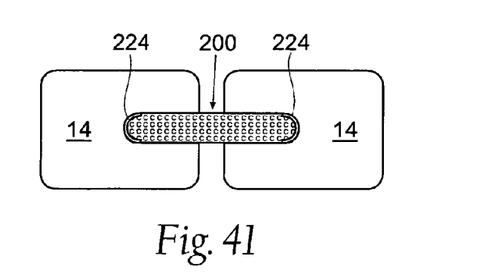
FIG. 41 is a front plan view illustrating the placement of the bone fixation/fusion device into the cavity within the restraints.

An alternative embodiment is illustrated in FIGS. 40 and 41. In this embodiment, a c-shaped restraint 224 is placed against each end of the bored cavity 222. The selected bone fixation/fusion device 200 is then positioned between the restraints 222 such that the restraints 222 engage the device 200 to secure the device 200 within bone.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A method comprising
identifying a bone site comprising a first bone segment, a second bone segment, and a non-bony region comprising an interruption between the first and second bone segments,
providing a rectangular bone fixation/fusion device comprising first and second rectangular surfaces and edge surfaces extending from the rectangular surfaces to form a rectangular wafer, and an elongated fixating ridge projecting from at least one of the rectangular surfaces,
forming a first cavity in the first bone segment that extends along one side of the interruption to receive an edge surface of the rectangular wafer,
forming a second cavity in the second bone segment that extends along another side of the interruption to receive another edge surface of the rectangular wafer, the second cavity generally facing the first cavity across the interruption,
positioning the rectangular wafer across the interruption between the first and second bone segments by inserting edge surfaces of the rectangular wafer into the first cavity and the second cavity, and
stabilizing the bone site by gripping the elongated fixation ridge into bone;
wherein at least one of the edge surfaces includes a guide bore, and
wherein the positioning includes placing a guide pin in one of the first and second cavities, and passing the guide bore over the guide pin to insert the at least one edge surface into the cavity.

2. A method according to claim 1
further including providing first and second restraints, and
wherein the positioning includes placing the first and second restraints, respectively, in the first and second cavities, and inserting edge surfaces of the rectangular bone fixation device into the restraints.

3. The method according to claim 2, wherein the first and second restraints have a substantially c-shape defining a channel for receiving the edge surfaces of the bone fixation device.

4. A method according to claim 1
wherein at least one of the first and second rectangular surfaces includes a region permitting bony in-growth and/or through growth.

* * * * *